(12) United States Patent
Mandelkorn

(10) Patent No.: US 6,371,122 B1
(45) Date of Patent: Apr. 16, 2002

(54) GAUGE/DILATOR APPARATUS

(76) Inventor: Robert M. Mandelkorn, 6315 Forbes Ave., Pittsburgh, PA (US) 15217

(*) Notice: Subject to any disclaimer, the term of this patent is extended or adjusted under 35 U.S.C. 154(b) by 0 days.

(21) Appl. No.: 09/597,480

(22) Filed: Jun. 20, 2000

(51) Int. Cl.⁷ .................................................. A61B 17/00
(52) U.S. Cl. ........................................ 128/887; 604/8
(58) Field of Search ................... 128/846, 848, 128/887; 604/4, 8, 9, 10

(56) References Cited

U.S. PATENT DOCUMENTS

| 3,949,750 A | 4/1976 | Freeman |
| 4,959,048 A * | 9/1990 | Seder .............................. 604/9 |
| 5,283,063 A | 2/1994 | Freeman |
| 5,318,513 A | 6/1994 | Lieb et al. |
| 5,417,651 A | 5/1995 | Guena et al. |
| 5,423,777 A | 6/1995 | Tajiri et al. |
| 5,723,005 A | 3/1998 | Herrick |
| 5,741,292 A | 4/1998 | Mendius |
| 6,016,806 A | 1/2000 | Webb |
| 6,027,470 A | 2/2000 | Mendius |
| 6,041,785 A | 3/2000 | Webb |
| 6,234,175 B1 * | 5/2001 | Zhou ........................... 128/887 |

* cited by examiner

Primary Examiner—Michael A. Brown
(74) Attorney, Agent, or Firm—Davidson, Davidson & Kappel, LLC

(57) ABSTRACT

An apparatus for measuring a lacrimal punctum and a canaliculus is provided. The apparatus comprises a handle and a tip disposed at one end of the hand, said tip having a gauge portion of size and shape to allow measurement of the lacrimal punctum and the canaliculus. The apparatus may further comprise a dilator portion disposed between the gauge portion and handle.

12 Claims, 5 Drawing Sheets

GAUGE/DILATOR APPARATUS

FIELD OF THE INVENTION

The present invention is related to the field of keratoconjunctivitis sicca, and specifically to an apparatus for determining the proper size of a punctum plug to be used in treating dry eye.

BACKGROUND OF THE INVENTION

Keratoconjunctivitis sicca (commonly known as "dry eye") is a chronic, bilateral dryness of the conjunctiva and cornea, marked by hyperemia of the conjunctiva, lacrimal deficiency, thickening of the corneal epithelium, itching and burning of the eye, and often reduced visual acuity (Saunders, W. B., *Dorland's Illustrated Medical Dictionary*, 27$^{th}$ Edition, Harcourt Brace Jovanovich, Inc., Philadelphia, Pa., 1988, page 874). As an isolated phenomenon or in association with systemic diseases, dryness of the eyes occurs when the moisture level in the eye is not maintained by the balance of tear production and tear loss through drainage and evaporation.

Causes of dry eye include aging, hormonal change, a disease state, a medication, a contact lens, or a change in the environment.

In treating dry eye, it is desirable to determine a long term solution which provides for retention of a patient's lacrimal fluid using minimally invasive means. Several methods of treatment are available.

For example, one method of treatment replaces the natural tears using artificial tears. Artificial tears provide temporary relief for dry eyes, but with prolonged use can actually disrupt the eye's natural production of tears and lead to further aggravation of the dry eye condition by washing away the natural infection fighting tear film on the eye. (Berkow, R. and Fletcher, A. J., *The Merck Manual*, 16$^{th}$ Edition, Merck Research Laboratories, Rahway, N.J., 1992, page 2374).

Another method of treatment involves permanent occlusion of the lacrimal punctum (also referred to as "punctum opening"). The occlusion prevents the lacrimal fluid from draining, thereby allowing the eyes to remain moist. Occlusion of the lacrimal punctum has been achieved using non-reversible cautery or laser closure to block lacrimal fluid drainage to the lacrimal canaliculi (tear drainage duct) and in severe cases partial tarsorrhapy is used to reduce loss of tears through evaporation.

Yet another method of treatment involves blocking drainage of lacrimal fluid by temporary non-surgical means, e.g., by use of a punctum plug.

U.S. Pat. No. 3,949,750 to Freeman (issued 1976), incorporated herein by reference, describes a removable rod-like plug for blocking lacrimal fluid flow through the punctum and associated canaliculus of the eye. Insertion of the plug is achieved by first dilating the punctal opening and canaliculus to about three times normal size followed by plug insertion.

Various removable punctum plugs and their use are also described in a number of patents, including: U.S. Pat. No. 5,283,063 to Freeman, issued 1994; U.S. Pat. No. 5,423,777 to Tajiri, issued 1995; U.S. Pat. No. 5,741,292 to Mendius, issued 1998; U.S. Pat. No. 5,318,513 to Lieb, et al., issued 1994; U.S. Pat. No. 5,417,651 to Guena, et al., issued 1995; U.S. Pat. No. 5,723,005 to Herrick, issued 1998; U.S. Pat. No. 6,016,806 to Webb, issued 2000; U.S. Pat. No. 6,041,785 to Webb, issued 2000; and U.S. Pat. No. 6,027,470 to Mendius, issued 2000. Each of the above patents are hereby incorporated by reference.

The punctum plugs can be utilized to close the upper as well as the lower punctal opening. The plugs were meant to firmly seat in the lacrimal punctum, being held in place by the punctal sphincter. In practice, however, they are known to fall out from the punctal opening or pass downward through the canaliculus, causing impassable canalicular stenoses. This occurs when the plug used is too small. On the other hand, too large a plug causes discomfort. Accordingly, determining the right size of the punctum plug to be used for occlusion of the punctum opening is important for successful treatment of dry eye.

SUMMARY OF THE INVENTION

It is an object of the present invention to provide an apparatus for determining the appropriate size of a punctum plug to be used in blocking a lacrimal punctum.

It is an object of the present invention to provide an apparatus for measuring a lacrimal punctum and canaliculus.

It is a further object of the present invention to provide an apparatus for controlled dilation of a punctum and a canaliculus to facilitate insertion of a punctum plug into the lacrimal punctum.

It is a further object of the present invention to provide a method for determining the appropriate size of a punctum plug to be used in blocking a lacrimal punctum.

In accordance with the above-identified objects and others, the present invention is related to an apparatus comprising a handle and a tip positioned at one end of the handle, said tip comprising a gauge (also referred to as "gauge portion") having a shape and size that allows measurement of a lacrimal punctum as well as the canaliculus associated with said lacrimal punctum.

The gauge may be used to make an accurate measurement of the size (e.g., diameter) of the lacrimal punctum and canaliculus, which in turn allows one to determine what size punctum plug to be used. When a punctum plug is inserted into a lacrimal punctum, at least a portion of it rests on the canaliculus. By measuring the size of the canaliculus, in addition to the lacrimal punctum, and selecting for a plug which at will rest within the lacrimal punctum and the canaliculus and has approximately the same size diameter as the lacrimal punctum and the canaliculus, one can select a better fitting plug. For example, if the canaliculus measured is about 0.7 mm in diameter, a punctum plug of 0.7 mm diameter would be appropriate.

In an embodiment of the invention, the gauge has a plurality of graduating diameters each diameter corresponding to a respective lacrimal punctum and a canaliculus. The gauge can be conical in shape with the gauge gradually increasing in diameter from 0.1 to 1.0 mm and is at least 1.5–2.0 mm in length. One may use the apparatus of the present invention as follows. Insert the tip into the punctal opening slowly inserting apparatus into punctal opening until the sphincter seats flush around the smallest diameter of the handle. Read the marked graduation at this point. At this point, it is recommended that the tip not be inserted farther into the canaliculus, as doing so may cause premature or over-dilation of the sphincter.

In an embodiment, the gauge portion of the apparatus is of cylindrical shape. In an embodiment the gauge has a diameter of about 0.1 mm to about 1.0 mm and a length of 2 mm to 10 cm. In preferred embodiments, the gauge is at least 0.5–2 mm in length and about 0.4–0.9 mm in diameter.

Preferably, the tip further comprises a tapered end, located at the end of the gauge, which may facilitate the insertion of the gauge into the punctum opening.

In preferred embodiments of the invention, the tip portion of the apparatus further comprises a dilator (also referred to as "dilator portion") disposed between the gauge and the handle. After the lacrimal punctum and the canaliculus are measured using the gauge, the dilator portion is inserted into the puncture to dilate it to facilitate the insertion of the plug. Preferably, the dilator is of cylindrical shape and have a diameter that is about 0.1 mm larger than the diameter of the gauge.

In certain embodiments, the apparatus of the present invention further comprises a second tip on the other end of the handle. Accordingly, the apparatus comprises a handle, with a first tip having a first gauge disposed on one end of the handle and a second tip having a second gauge being disposed on the other end of the handle.

In addition, the apparatus may further comprise a first dilator located between the first gauge and the handle, and a second dilator located between the second gauge and the handle. A tapered tip may be provided at the end of the first and the second gauge to facilitate the insertion of the gauge. For example, one handle may contain the first gauge of about 0.4 mm in diameter and the second gauge of about 0.5 mm in diameter; another may contain the first gauge of about 0.6 mm in diameter and the second gauge of about 0.7 mm in diameter; and yet another may contain the first gauge of about 0.8 mm in diameter and the second gauge of about 0.9 mm in diameter.

In accordance with the embodiments of the invention, set forth are illustrative size and shape gauge that may be used in an embodiment of this invention, however any size or shape gauge that allows measurement of a lacrimal punctum and a canaliculus are included in this invention.

The present invention also relates to a plurality of measurement devices, each device comprising a handle and a tip disposed at the end of the handle, said tip comprising a gauge having a shape and size that allows measurement of a lacrimal punctum and a canaliculus, each gauge having a different diameter, wherein the different diameters incrementally increase 0.1 mm from a first gauge to a last gauge of the plurality of gauges. For example, one may use the apparatus of the present invention as follows. Starting with the smallest size gauge apparatus insert the gauge portion of the tip into the punctal opening until the sphincter seats flush around the smallest diameter of the handle and short of the dilator portion of the tip. If the gauge portion tested appears to enter the lacrimal punctum with little or no resistance, it is too small. Likewise, if a large gauge offers substantial resistance, it is too large. Proceed to the next larger size apparatus until the gauge portion fits snugly when both entering and exiting the punctal opening.

In certain embodiments, the apparatus of the present invention further comprises a punctum plug disposed at the other end of the handle. For example, the apparatus comprises a handle having a gauge (or gauge and dilator) at one end of said handle and a plug removably disposed on the other end. In preferred embodiments, the gauge and the plug are of the same diameter.

In certain embodiments, the apparatus of the present invention comprises a handle and a tip disposed on the end of the handle, said tip comprising a gauge portion. Such apparatus may comprise a series of handles with gauges of 0.1 mm increments, from 0.4 to 0.9 mm in diameter. Such apparatus my comprise a dilator portion.

The apparatus of the present invention may be producing using, e.g., an alloy of stainless steel, polytetrafluorethylene, hydroxyethylnethacrylate, a hydrophilic polymer, or any metal or plastic tissue-inert material. In certain embodiments of the invention, the apparatus handle and the tip are autoclavable. In certain embodiments of the invention, the apparatus is disposable.

The present invention further provides a method for measuring a lacrimal punctum and associated canaliculus. The method comprises, inserting the gauge of the apparatus into a lacrimal punctum until a sphincter seats flush around the tip and by this means measuring the lacrimal punctum and canaliculus.

In an embodiment the gauge/dilator system is designed to aid the physician in determining the proper size punctum plug for use. Additionally, once the plug size is determined, each apparatus provides a simple and controlled method for punctal dilation prior to insertion of a sized punctum plug. Application of a topical anesthetic to the punctum is important. For example, one may use the apparatus of the present invention as follows. Starting with the smallest size gauge insert the gauge portion of the tip into the punctal opening until the sphincter seats flush around the smallest diameter of the handle and short of the dilatorportion of the tip. At this point, it is recommended that the tip not be inserted further into the canaliculus, as doing so may cause premature or over-dilation of the sphincter. If the gauge portion tested appears to enter the lacrimal punctum with little or no resistance, it is too small. Likewise, if a large gauge offers substantial resistance, it is too large. Proceed to the next larger size until the gauge portion fits snugly when both entering and exiting the punctal opening.

In accordance with this invention the punctum plug is inserted into the lacrimal punctum.

As used herein the word "diameter" indicates the diameter of a circular, cylindrical or conical object as well as the width of a non-circular object, for example a pyramid.

The foregoing and other objectives, features and advantages of the present invention will be more readily understood upon consideration of the following detailed description of the invention, taken in conjunction with the accompanying figures.

DETAILED DESCRIPTION OF THE PREFERRED EMBODIMENTS

The eye contains round or slightly ovoid openings approximately 0.3 mm in size (lacrimal punctum or punctal opening) and surrounded by connective tissue (sphincter)

about 1 mm in depth. Each of the punctal openings leads into a vertical portion of the respective canaliculus, which is about 2.5 to 3.5 mm in length, before turning horizontally for about 8 mm to join its other canaliculus at the entrance of a lacrimal sac.

Figure 1:
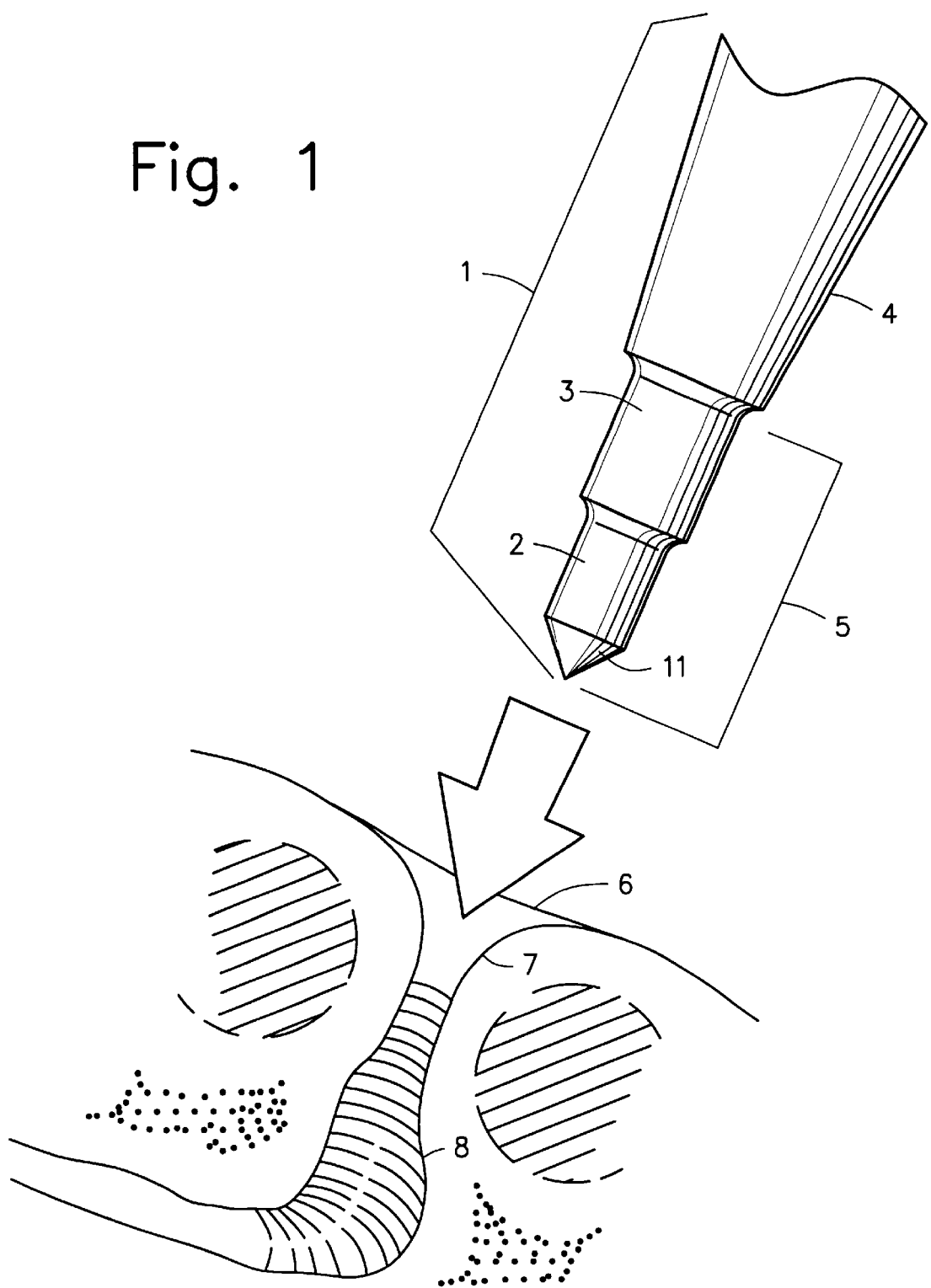
FIG. 1 shows a partial view of an apparatus according to the present invention, specifically showing a tip and a portion of a handle.

Referring to FIG. 1, there is shown a representation of an apparatus 1 according to the present invention for sizing and dilating a lacrimal punctum 6. Apparatus 1 comprises a handle 4 and a tip 5.

The tip 5 has a dilator portion 3 and a gauge portion 2. The gauge portion 2 is of cylindrical shape, has a diameter ranging from about 0.1–1.0 mm (preferably from about 0.4 mm to about 0.9 mm) and is of 0.5 mm to about 2 mm in length (preferably about 2 mm). Tapered tip 11 located at the end of the gauge portion 2 facilitates the insertion of the gauge into the lacrimal punctum. The dilator portion 3 has a diameter that is about 0.1 mm larger than the diameter of the gauge portion 2. This graduated system provides for actual measurement of the lacrimal punctum 6 and canaliculus 8 (e.g., the vertical portion of the canaliculus) with the gauge 2 followed by insertion of the dilator 3 to provide a controlled dilation of the punctal dilation prior to insertion of a punctum plug.

Figure 2:
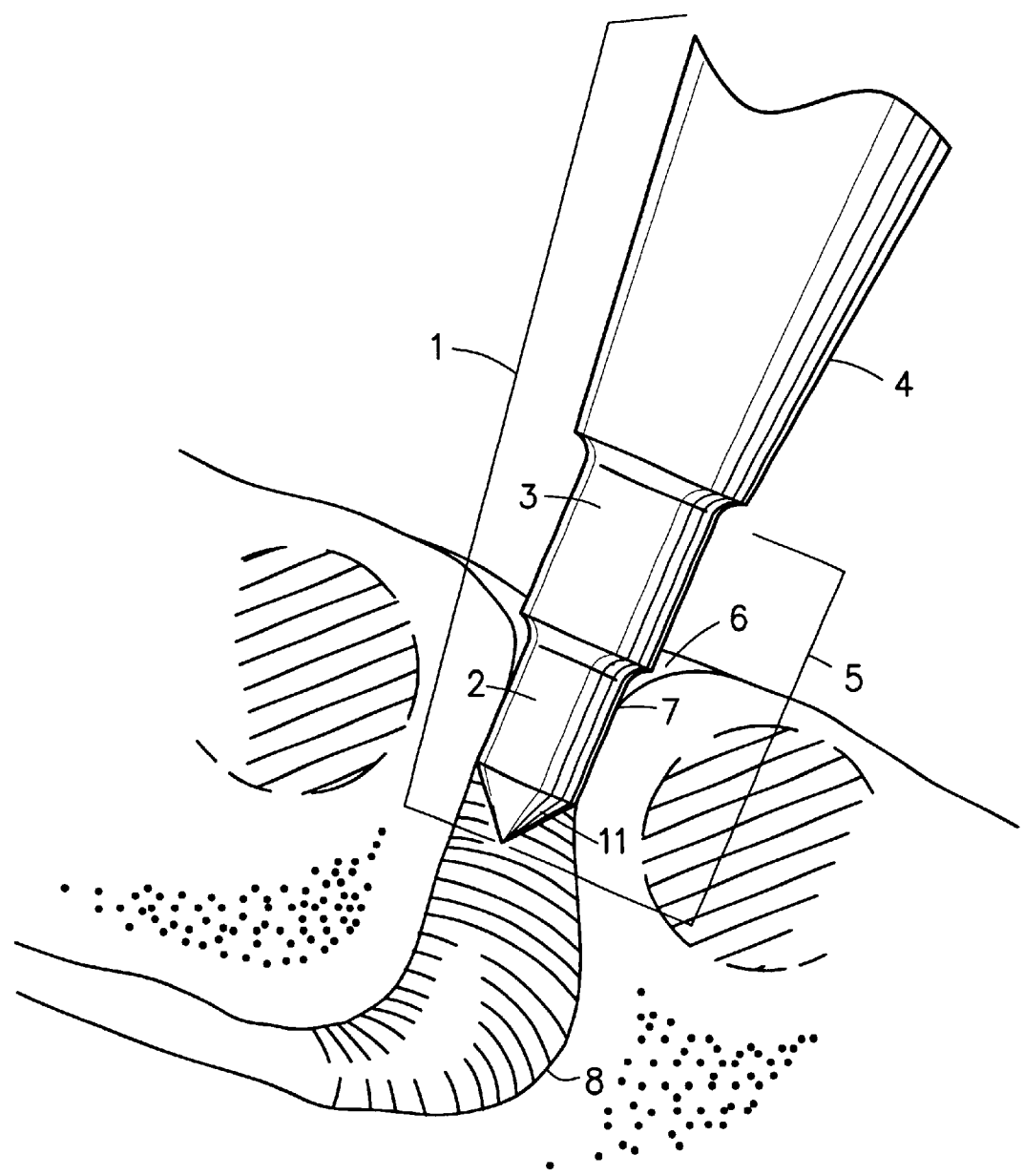
FIG. 2 shows the insertion of the gauge portion of the tip into the lacrimal punctum, specifically showing the sphincter seated flush (snugly) around the gauge portion.
Figure 3:
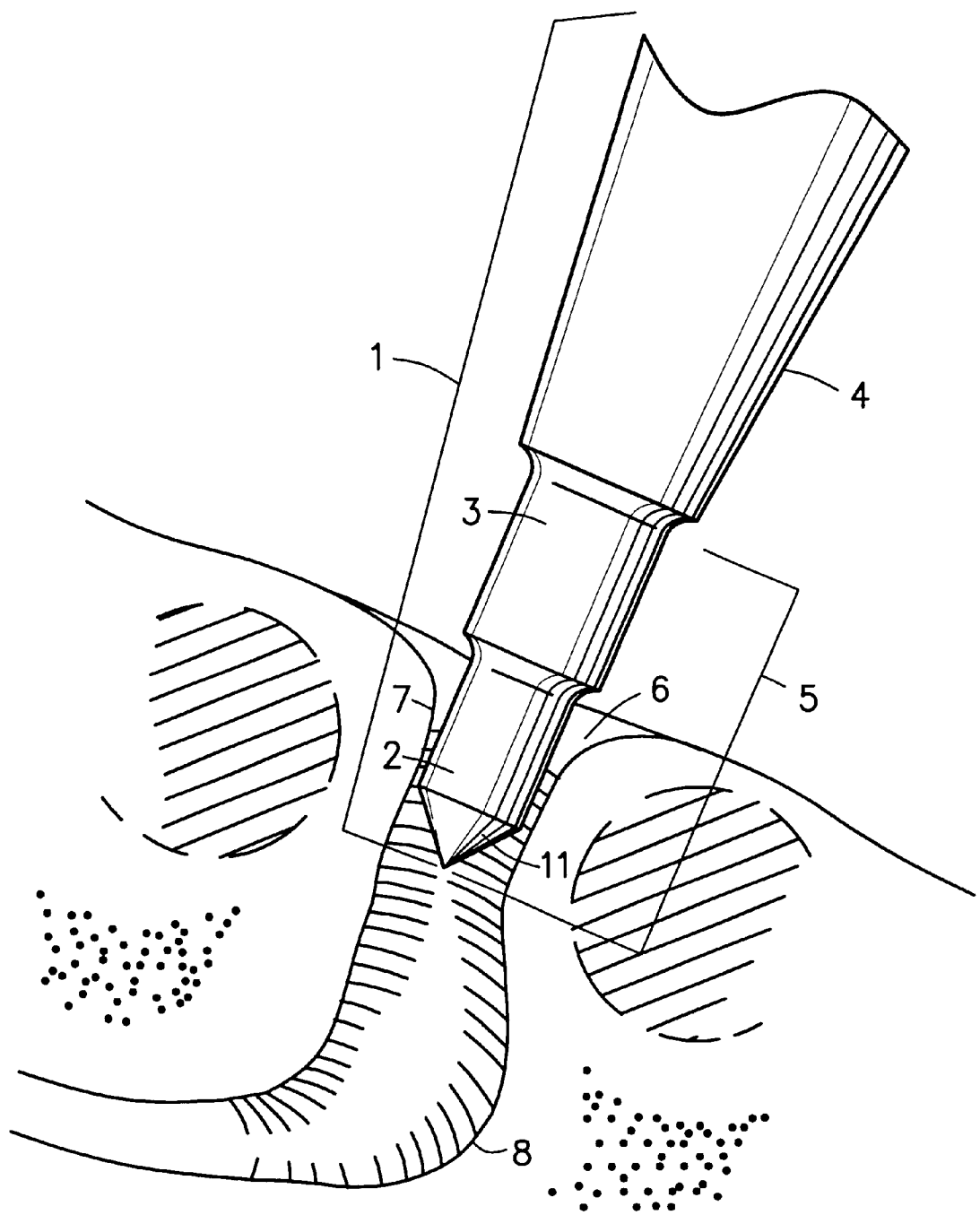
FIG. 3 shows the insertion of the gauge portion where there is little or no resistance between the gauge portion and the sphincter.
Figure 4:
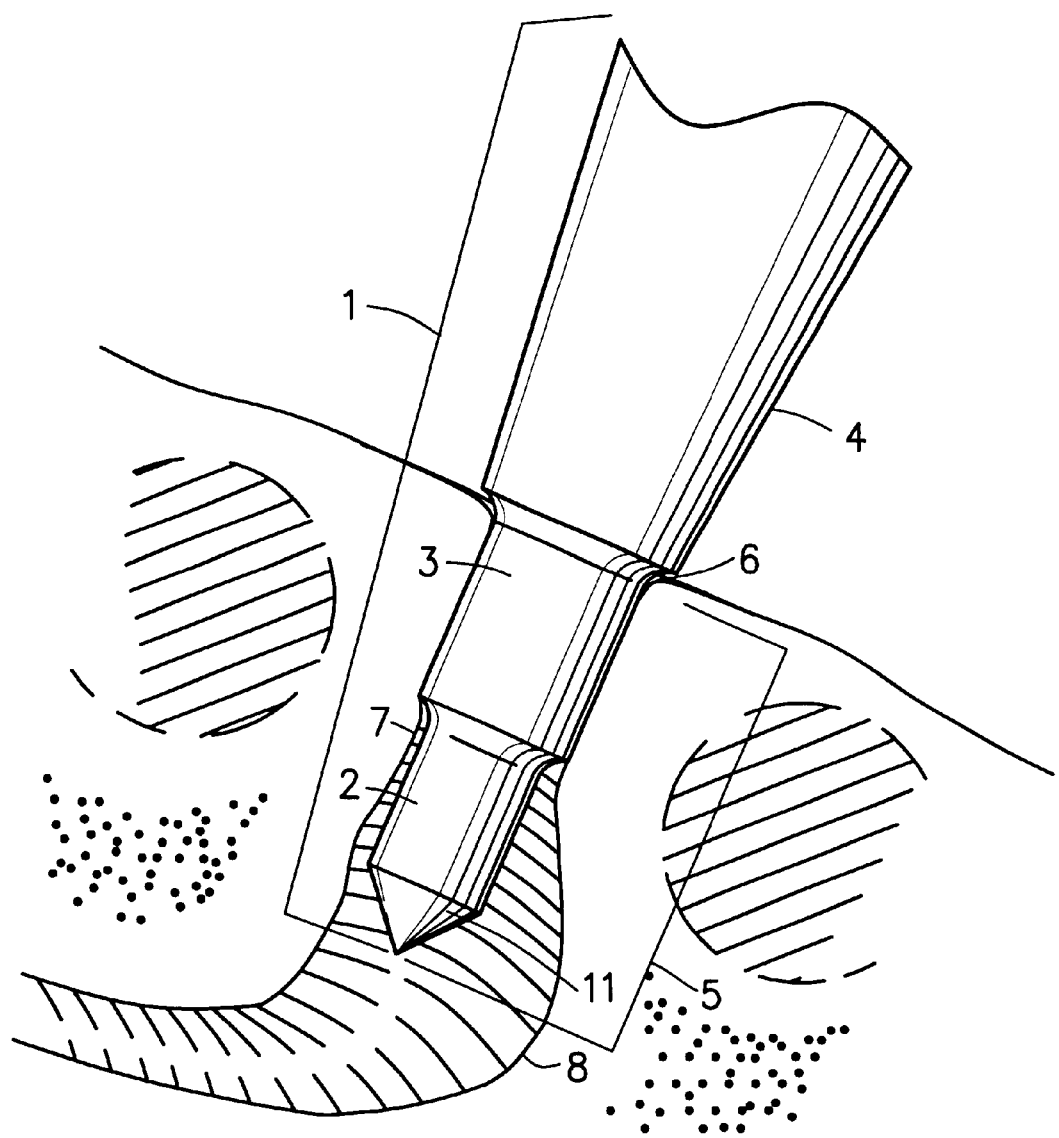
FIG. 4 shows the insertion of the dilator and gauge portion of the tip into the lacrimal punctum for controlled dilation of the sphincter.
Figure 5:
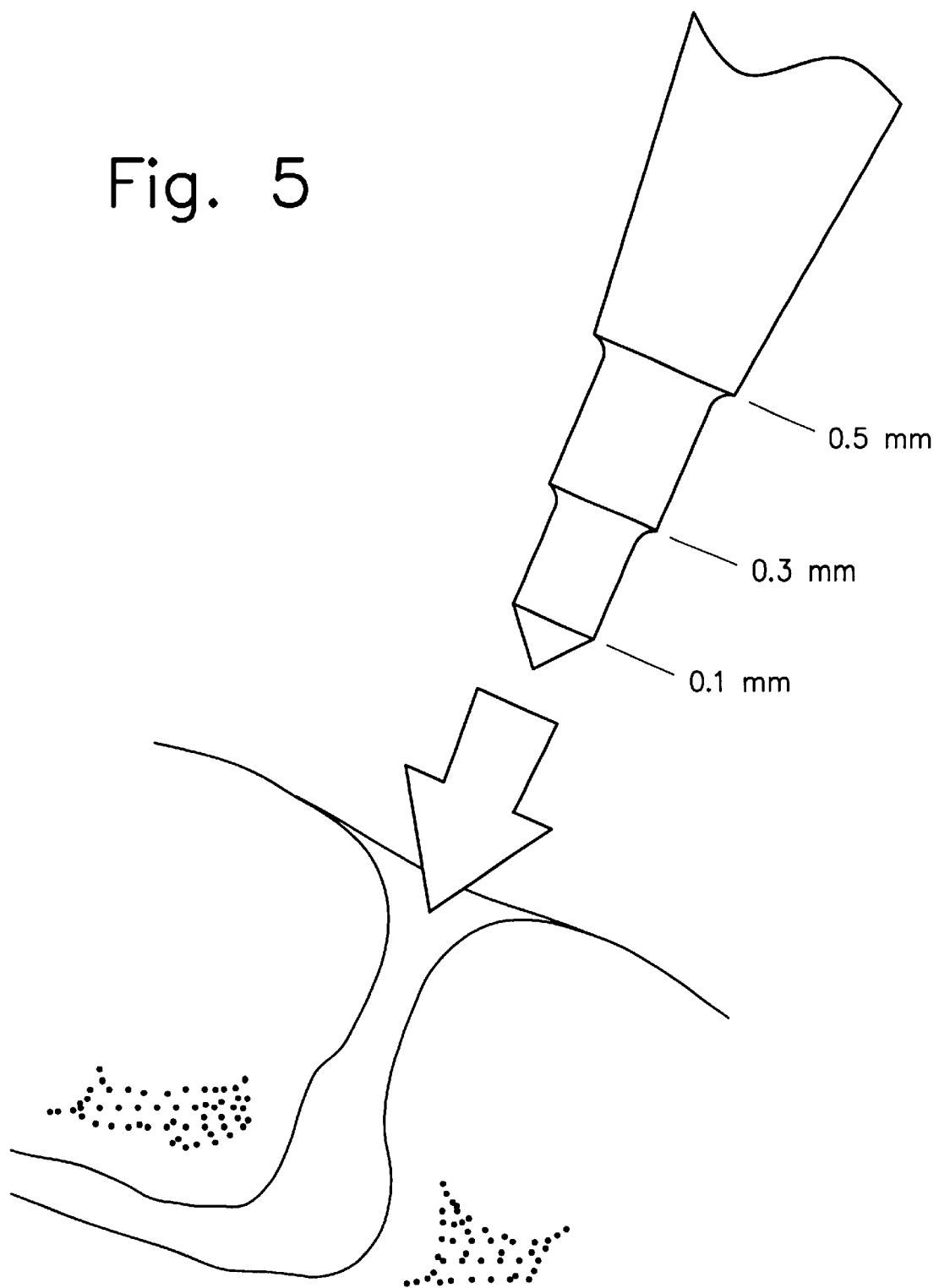
FIG. 5 shows a partial view of an apparatus according to the present invention specifically showing a gauge having a plurality of graduating diameters.

As previously described, in the treatment of keratoconjunctvitis sicca prevention of the drainage of lacrimal fluid from the eye may be achieved by blocking the lacrimal punctum 6. FIGS. 2, 3 and 4 depict a method for proper measurement of the lacrimal punctum and canaliculus, and dilation of the punctum, prior to insertion of a punctum plug.

Referring to FIG. 2 which depicts proper insertion of the gauge portion 2, e.g., it is inserted into the lacrimal punctum 6 until the sphincter 7 seats flush around the gauge portion 2 providing a snug fit. In the preferred embodiment a series of gauge portion 2 of the tip 5 ranging from 0.4 to 0.9 mm are used to measure the lacrimal punctum 6 and canaliculus 8. By inserting the gauge portion 2 of the tip 5 into the lacrimal punctum 6 and canaliculus 8 in a graduated fashion from the smallest gauge to the largest gauge, a snug fit can be observed and measured. The gauge size that provides the snug fit is then used to determine the correct size punctum plug to use. When performing the measurement step, it is important to observe the seating of the gauge portion 2 without advancing the tip 5 farther into the canaliculus 8, as doing so may cause premature or over-dilation of the sphincter.

Referring to FIG. 3 which depicts insertion of the tip into the lacrimal punctum 6. When the gauge portion 2 of the tip 9 appears to enter the sphincter 7 with little or no resistance, the gauge is too small and the next largest size gauge should be used. It is recommended that the next gauge tested be about 0.1 mm larger than the previous gauge used. Alternatively, if the gauge portion 2 offers substantial resistance when entering the lacrimal punctum 6, it is to large. The next smallest gauge should be tested. Continue insertion of the gauge portion 2 incrementally with the next gauge until the gauge portion 2 of the tip 5 fits snugly.

Referring to FIG. 4, which depicts controlled punctal dilation, the dilator portion 3 of the tip 5 may be inserted in the lacrimal punctum 6. Insertion of the dilator 3 results in a controlled dilation of the sphincter 7. Once sphincter dilation is observed remove the tip 5. Insert a punctum plug into the lacrimal punctum following insertion instructions for the specific punctum plug used. Insertion of the punctum plug is done as quickly as possible to ensure dilation of the sphincter.

In describing the invention, reference has been made to a preferred embodiment and illustrative advantages of the invention. Those skilled in the art, however, may recognize additions, deletions, modifications, substitutions and other changes which will fall within the purview of the subject invention and claims.

What is claimed is:

1. An apparatus for measuring a lacrimal punctum and a canaliculus comprising a handle and a tip disposed at the end of the handle, said tip comprising a gauge having a shape and size that allows measurement of a lacrimal punctum and a canaliculus, wherein said tip further includes a dilator disposed between the handle and the gauge and having a diameter that is about 0.5–2 mm larger than the diameter of the gauge.

2. The apparatus of claim 1, wherein the dilator is about 1 mm–3 mm in length.

3. An apparatus for measuring a lacrimal punctum and a canaliculus comprising a handle, a first tip having a first gauge on one end of the handle and a second tip having a second gauge on the opposite end of the handle, each gauge having a shape and size that allows measurement of a lacrimal punctum and a canaliculus.

4. The apparatus of claim 3, wherein the first gauge and the second gauge have a diameter of about 0.1 mm to about 1.0 mm, and wherein the diameter of the first gauge is different from the diameter of the second gauge.

5. The apparatus of claim 3, wherein the diameter of the first gauge is different from the diameter of the second gauge by 0.1 mm increments.

6. The apparatus of claim 3, further comprising a first dilator located between the first gauge and the handle, and a second dilator between the second gauge and the handle.

7. The apparatus of claim 3, wherein the first gauge is about 0.4 mm in diameter and the second gauge is about of 0.5 mm in diameter.

8. The apparatus of claim 3, wherein the first gauge is about 0.5 mm in diameter and the second gauge is about of 0.6 mm in diameter.

9. The apparatus of claim 3, wherein the first gauge is about 0.6 mm in diameter and the second gauge is about 0.7 mm in diameter.

10. The apparatus of claim 3, wherein the first gauge os about of 0.8 mm in diameter and the second gauge is about 0.9 mm in diameter.

11. An apparatus for measuring a lacrimal punctum and a canaliculus comprising a handle and a tip disposed at the end of the handle, said tip comprising a gauge having a shape and size that allows measurement of a lacrimal punctum and a canaliculus, wherein the apparatus further includes a punctum plug on the opposite end of the handle, said punctum plug and the gauge having the same diameter.

12. A method for treating keratoconjunctivitis sicca, comprising the steps of:
   a) inserting the gauge portion of the apparatus of claim 1, into a lacrimal punctum until a sphincter seats flush around the gauge portion when observed and by this means determining whether the inserted gauge portion fits snugly when both entering and exiting the lacrimal punctum;
   b) inserting a larger or smaller diameter gauge portion of the apparatus into the lacrimal punctum if the gauge portion in step (a) does not fit snugly or offers to much resistance when inserted and repeating step (a) with increasingly larger or smaller diameter gauge portions until the sphincter is observed to fit snugly;
   c) inserting a dilator portion into the lacrimal punctum without first removing the gauge portion in step (b);
   d) removing the apparatus from the lacrimal punctum and immediately inserting a punctum plug the same size as the largest gauge portion used in steps (b) or (c) into the lacrimal punctum thereby treating keratoconjunctivitis sicca.

* * * * *